(12) United States Patent
Goates et al.

(10) Patent No.: US 8,162,913 B2
(45) Date of Patent: Apr. 24, 2012

(54) FOLDED ABSORBENT ARTICLE

(75) Inventors: Michael J. Goates, Brigham City, UT (US); Eric I. Schields, Eden, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1632 days.

(21) Appl. No.: 11/281,765

(22) Filed: Nov. 16, 2005

(65) Prior Publication Data
US 2007/0112321 A1 May 17, 2007

(51) Int. Cl.
*A61F 13/15* (2006.01)
(52) U.S. Cl. ....... 604/385.201; 604/385.01; 604/385.13; 604/385.101
(58) Field of Classification Search ........... 604/385.201, 604/385.01, 385.13, 385.101
See application file for complete search history.

(56) References Cited

U.S. PATENT DOCUMENTS

| | | | |
|---|---|---|---|
| 3,863,637 A * | 2/1975 | MacDonald et al. ......... 604/365 |
| 4,663,220 A | 5/1987 | Wisneski et al. |
| 4,704,116 A | 11/1987 | Enloe |
| 4,798,603 A | 1/1989 | Meyer et al. |
| 5,114,781 A | 5/1992 | Morman |
| 5,116,662 A | 5/1992 | Morman |
| 5,176,668 A | 1/1993 | Bernardin |
| 5,192,606 A | 3/1993 | Proxmire et al. |
| 5,226,992 A | 7/1993 | Morman |
| 5,486,166 A | 1/1996 | Bishop et al. |
| 5,490,846 A | 2/1996 | Ellis et al. |
| 5,496,298 A | 3/1996 | Kuepper et al. |
| 5,509,915 A | 4/1996 | Hanson et al. |
| 5,645,542 A | 7/1997 | Anjur et al. |
| 5,883,028 A | 3/1999 | Morman et al. |
| 5,964,743 A | 10/1999 | Abuto et al. |
| 6,231,557 B1 | 5/2001 | Krautkramer et al. |
| 6,318,555 B1 | 11/2001 | Kuske et al. |
| 6,362,389 B1 | 3/2002 | McDowall et al. |
| 6,461,343 B1 | 10/2002 | Schaefer et al. |
| 6,552,245 B1 | 4/2003 | Roessler et al. |
| 2004/0167489 A1 | 8/2004 | Kellenberger et al. |
| 2005/0256495 A1 | 11/2005 | Schlinz et al. |
| 2006/0246248 A1 | 11/2006 | Van Dyke |
| 2006/0247596 A1 | 11/2006 | Van Dyke |

FOREIGN PATENT DOCUMENTS

| | | |
|---|---|---|
| EP | 0 217 032 A2 | 4/1987 |
| EP | 0 947 446 A1 | 10/1999 |
| EP | 1 166 735 A2 | 1/2002 |
| WO | WO 91/08962 A1 | 6/1991 |
| WO | WO 01/88245 A2 | 11/2001 |
| WO | WO 2003/051254 | 6/2003 |
| WO | WO 2004/073570 A1 | 9/2004 |
| WO | WO 2005/110321 A1 | 11/2005 |

* cited by examiner

*Primary Examiner* — Jacqueline F. Stephens
(74) *Attorney, Agent, or Firm* — John L. Brodersen; Randall W. Fieldback

(57) ABSTRACT

An absorbent article includes an absorbent chassis, a first ear and a first fastening member. The absorbent article can also include a plurality of folds. The plurality of folds can arrange the fastening member in an overlaid relationship with said inner surface on said absorbent chassis.

20 Claims, 7 Drawing Sheets

FOLDED ABSORBENT ARTICLE

BACKGROUND OF THE INVENTION

The present invention relates to absorbent articles. More specifically, the invention relates to an absorbent article, such as a disposable diaper, that includes a pair of ears and that is configured to provide a product that can more readily retain its appearance during processing and packaging.

Absorbent articles such as disposable diapers are typically made on high speed (i.e., hundreds of products per minute) production lines. When manufacturing articles in this way, it is desirable to produce a product that includes features that provide an attractive product to the caregiver and/or the user and that is effective at containing and absorbing bodily exudates. An example of such features includes separately attached ears. The ears can be useful for providing better hip coverage to the wearer. Further, the ears can optionally be stretchable or even elastomeric for improved fit and comfort. Moreover, the ears can include a fastening member to keep the article about the hips and waist of the wearer.

While absorbent articles that include features such as separately attached ears can be desirable to consumers, such articles can become creased and/or undesirably wrinkled or crumpled during the production and/or packaging due at least in part to the difficulty in controlling such features during the manufacturing process and during packaging. This can result in a product that may be less attractive to the consumer when it is removed from the package. Moreover, the performance of the product can potentially be compromised; for example if a fastening member is creased it can compromise its ability to engage with different portions of the article as intended.

Thus, there is a need for an absorbent article that includes a folding configuration that can protect product features such as ears and/or fasteners. Further, there is a need for such an article that includes a folding configuration that can be processed at high speeds. Still further, there is a need for such an article that is pleasing to the wearer and/or caregiver upon being removed from a package.

SUMMARY OF THE INVENTION

In one aspect, the present invention is directed to a folded absorbent article. The folded absorbent article defines a lateral direction and a longitudinal direction perpendicular to the lateral direction, and an inner surface and an outer surface opposite the inner surface. The folded absorbent article includes an absorbent chassis defining a chassis back waist edge and a chassis front waist edge opposite the chassis back waist edge, a first chassis side edge extending in the longitudinal direction and a second chassis side edge extending in the longitudinal direction opposite the first chassis side edge. The absorbent chassis includes a liquid impermeable outercover and an absorbent body disposed on the outercover. The folded absorbent article further includes a first ear formed separately from and attached proximate the first chassis side edge and a first fastening member defining a first active fastening portion. The first fastening member is disposed on the first ear, where the first active fastening portion is in an overlaid relationship with the inner surface on the first ear. The folded absorbent article also includes a first inboard fold where the first fastening member is in an overlaid relationship with the inner surface on the absorbent chassis proximate the first chassis side edge and defines a first inboard fold width in the lateral direction. The folded absorbent article also includes a first interior fold defining a first interior fold axis inboard of the first chassis side edge, and a first interior fold width in the lateral direction, where the first interior fold width is at least as wide as the first inboard fold width.

In another aspect, the present invention is directed to a package of absorbent articles including a package and a plurality of absorbent articles. Each of the absorbent articles defines a lateral direction and a longitudinal direction perpendicular to the lateral direction, and an inner surface and an outer surface opposite the inner surface. Each of the absorbent articles includes an absorbent chassis defining a chassis back waist edge and a chassis front waist edge opposite the chassis back waist edge, a first chassis side edge extending in the longitudinal direction and a second chassis side edge extending in the longitudinal direction opposite the first chassis side edge. The absorbent chassis includes a liquid impermeable outercover, and an absorbent body disposed on the outercover. Each of the absorbent articles also includes a first ear formed separately from and attached proximate the first chassis side edge and a first fastening member defining a first active fastening portion. The first fastening member is disposed on the first ear where the first active fastening portion is in an overlaid relationship with the inner surface on the first ear. Each of the absorbent articles also includes a first inboard fold where the first fastening member is in an overlaid relationship with the inner surface on the absorbent chassis proximate the first chassis side edge and defines a first inboard fold width in the lateral direction. Each of the absorbent articles also includes a first interior fold defining a first interior fold axis inboard of the first chassis side edge and a first interior fold width in the lateral direction where the first interior fold width is at least as wide as the first inboard fold width.

In yet another aspect, the present invention is directed to a folded absorbent article defining a lateral direction and a longitudinal direction perpendicular to the lateral direction, and an inner surface and an outer surface opposite the inner surface. The folded absorbent article includes an absorbent chassis defining a chassis back waist edge and a chassis front waist edge opposite the chassis back waist edge, a first chassis side edge extending in the longitudinal direction and a second chassis side edge extending in the longitudinal direction opposite the first chassis side edge. The absorbent chassis includes a liquid impermeable outercover and an absorbent body disposed on the outercover. The folded absorbent article also includes a first ear formed separately from and attached proximate the first chassis side edge, a second ear formed separately from and attached proximate the second chassis side edge. The folded absorbent article also includes a first fastening member defining a first active fastening portion, the first fastening member disposed on the first ear, and a second fastening member defining a second active fastening portion, the second fastening member disposed on the second ear. The folded absorbent article also includes a plurality of longitudinally extending folds. Accordingly, the outer surface on the first fastening member is in an overlaid relationship with the inner surface on the absorbent chassis proximate the first chassis side edge and the first ear is sandwiched by the inner surface of the absorbent chassis. In addition, the outer surface on the second fastening member is in an overlaid relationship with the inner surface on the absorbent chassis proximate the second chassis side edge and the second ear is sandwiched by the inner surface of the absorbent chassis.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

DEFINITIONS

Figure 1:
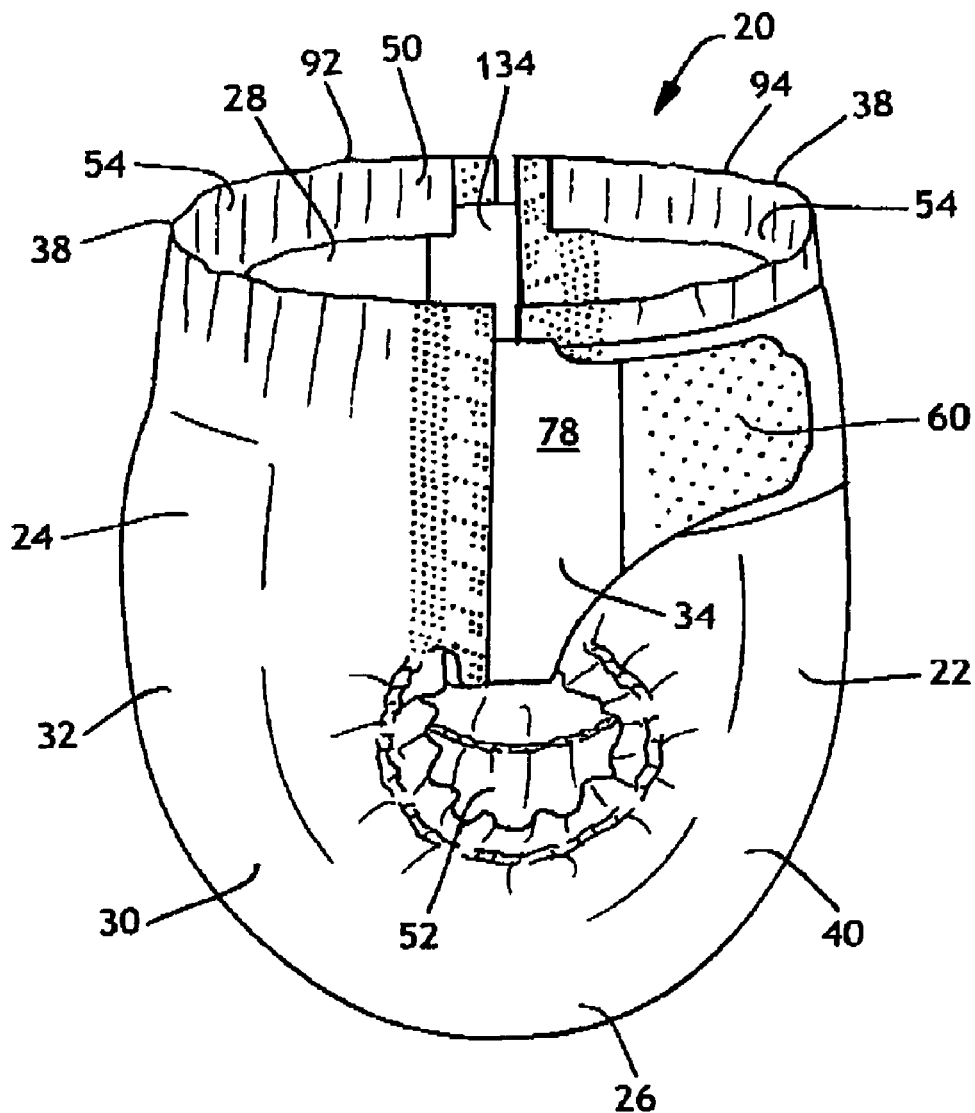
FIG. 1 representatively illustrates a side view of a diaper with a fastening member of the diaper in a fastened configuration.

Within the context of this specification, each term or phrase below includes the following meaning or meanings:

"Attach" and its derivatives refer to the adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Connect" and its derivatives refer to the adhering, bonding, attaching, sewing together, or the like, of two elements. Two elements will be considered to be connected together when they are integral with one another or connected directly to one another or indirectly to one another, such as when each is directly connected to intermediate elements. "Connect" and its derivatives include permanent, releasable, or refastenable connection.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 50 percent (to 150 percent) of its relaxed length.

"Fiber" refers to a continuous or discontinuous member having a high ratio of length to diameter or width. Thus, a fiber may be a filament, a thread, a strand, a yarn, or any other member or combination of these members.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Inboard" refers to a position relatively closer to the center of an absorbent garment, and particularly laterally and/or longitudinally closer to the longitudinal and lateral center of the absorbent garment.

"Join" and its derivatives refer to the adhering, bonding, sewing together, or the like, of two separate elements. Two elements will be considered to be joined together when they are joined directly to one another or indirectly to one another, such as when each is directly joined to intermediate elements. "Join" and its derivatives include permanent, releasable, or refastenable joinder.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Outboard" refers to a position relative to the center of an absorbent garment, and particularly laterally and/or longitudinally away from the longitudinal and lateral center of the absorbent garment.

"Overlaid" refers to the condition where one element is positioned to be at least partially covering or overlapping another element either directly or indirectly (i.e., other components or layers may be intermediate the overlaid elements). It should be noted that one element may be beneath the other element and still be overlaying the other element.

"Stretchable" means that a material can be stretched, without breaking, by at least 50 percent (to 150 percent of its initial (unstretched) length) in at least one direction. Elastic materials and extensible materials are each stretchable materials.

"Superabsorbent Material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Referring now to the drawings and in particular to FIG. 1, an absorbent article of the present invention is representatively illustrated in the form of baby diaper and is indicated in its entirety by the reference numeral 20. The diaper 20 can include a first ear 34 and a second ear 134. The diaper 20 can suitably be disposable, which refers to articles that are intended to be discarded after a limited period of use instead of being laundered or otherwise conditioned for reuse. It should also be understood that the present invention is suitable for use with various other absorbent articles intended for personal wear, including but not limited to children's training pants, feminine hygiene products, incontinence products, medical garments, surgical pads and bandages, other personal care or health care garments, and the like without departing from the scope of the present invention.

By way of illustration only, various materials and methods for constructing diapers such as the diapers 20 of the various aspects of the present invention are disclosed in U.S. patent application Ser. No. 10/836,490, filed Apr. 29, 2004, in the name of Schlinz et al.; U.S. Pat. No. 5,496,298 issued Mar. 5, 1996, to Kuepper et al.; U.S. Pat. No. 4,798,603 issued Jan. 17, 1989, to Meyer et al.; U.S. Pat. No. 5,176,668 issued Jan. 5, 1993, to Bernardin; U.S. Pat. No. 5,192,606 issued Mar. 9, 1993, to Proxmire et al., and U.S. Pat. No. 5,509,915 issued Apr. 23, 1996, to Hanson et al., each of which are incorporated herein by reference to the extent that they are consistent (i.e., not in conflict) herewith.

The diaper 20 is illustrated in FIG. 1 in a fastened condition. The diaper 20 defines a longitudinal direction 46 and a lateral direction 48 perpendicular to the longitudinal direction as shown in FIGS. 2-6. The diaper 20 further defines a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 includes those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The diaper 20 also define an inner surface 28 adapted in use to be disposed toward the wearer, and an outer surface 30 opposite the inner surface. With additional reference to FIGS. 2-6, the diaper 20 has a pair of opposed article side edges 36 extending in the longitudinal direction 46 and a pair of opposed article waist edges 38 extending in the lateral direction 48, referred to herein as the article back waist edge and the article front waist edge.

The illustrated diaper 20 can include an absorbent chassis, generally indicated at 32. The absorbent chassis 32 can define a first chassis side edge 90 extending in the longitudinal direction 46 and a second chassis side edge 91 extending in the longitudinal direction 46, opposite the first chassis side edge 90. The absorbent chassis 32 can also define a pair of longitudinally opposite chassis waist edges referred to herein as the chassis back waist edge 92 and the chassis front waist edge 94.

For example, in the aspect of FIGS. 1-6, the diaper 20 includes an absorbent chassis 32 and a first ear 34 formed separately from and attached to the absorbent chassis 32 proximate the first chassis side edge 90. The diaper 20 also can include a second ear 134 formed separately from and attached to the absorbent chassis 32 proximate the second chassis side edge 91. The ears 34, 134 can be attached along seams 56 proximate the chassis side edges 90, 91 in either the front waist region 22 or in the back waist region 24 of the diaper 20. In the illustrated aspects, the ears 34 and 134 are attached in the back waist region 24. The ears 34 and 134 may be attached to the absorbent chassis 32 using means known to those skilled in the art such as adhesive, thermal bonding, pressure bonding, ultrasonic bonding, and the like or combinations thereof.

The absorbent chassis 32 is illustrated in FIGS. 2-6 as being substantially I-shaped. However, it is contemplated that the absorbent chassis 32 may have other shapes (e.g., hourglass, T-shaped, rectangular, and the like) without departing from the scope of this invention.

The absorbent chassis 32 can include an outercover 40 and a bodyside liner 42 (FIG. 2) in a superposed relation therewith. The liner 42 can be suitably joined to the outercover 40 along at least a portion of the absorbent chassis 32. The liner 42 can be suitably adapted, i.e., positioned relative to the other components of the diaper 20, to contact the wearer's skin during wear of the diaper. The absorbent chassis 32 also includes an absorbent body 44 (FIG. 2) disposed on the inner surface of the article relative to the outercover 40 for absorbing liquid body exudates. For example, the absorbent body 44 can be located between the outercover 40 and the bodyside liner 42. The bodyside liner 42 and the outercover 40 can be attached to each other by adhesive, ultrasonic bonding, thermal bonding or by other suitable attachment techniques known in the art. Moreover, at least a portion of the absorbent body 44 can optionally be attached to the bodyside liner 42 and/or the outercover 40 utilizing the methods described above. The liner 42 can be coextensive with the outercover 40 or can be larger or smaller than the outercover 40.

The diaper 20 can optionally include a pair of containment flaps 55 for inhibiting the lateral flow of body exudates. The containment flaps 55 can be operatively attached to the diaper 20 in any suitable manner as is well known in the art. In particular, suitable constructions and arrangements for the containment flaps are generally well known to those skilled in the art and are described in U.S. Pat. No. 4,704,116 issued Nov. 3, 1987 to Enloe, which is incorporated herein by reference to the extent that it is consistent (i.e., not in conflict) herewith.

To further enhance containment and/or absorption of body exudates, the diaper 20 may optionally include waist elastic members 54 in the front and/or back waist regions 22 and 24 of the diaper 20. Likewise, the diaper 20 may optionally include leg elastic members 58, as are known to those skilled in the art. The waist elastic members 54 and the leg elastic members 58 can be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament spandex elastomeric threads sold under the trade name LYCRA and available from Invista of Wilmington, Del., U.S.A.

The outercover 40 may suitably include a material that is substantially liquid impermeable. The outercover 40 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 40 is a 0.025 millimeter (1.0 mil) polyethylene film commercially available from Edison Plastics Company of South Plainfield, N.J. Alternatively, the outercover 40 may include a woven or non-woven fibrous web layer that has been totally or partially constructed or treated to impart the desired levels of liquid impermeability to selected regions that are adjacent or proximate the absorbent body.

The outercover 40 may also be stretchable, and in some aspects it may be elastomeric. For example, such an outercover material can include a 0.3 osy polypropylene spunbond that is necked 60 percent in the lateral direction 40 and creped 60 percent in the longitudinal direction 48, laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outercover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent body 44. A suitable liquid permeable bodyside liner 42 is a nonwoven polyethylene/polypropylene bicomponent web having a basis weight of about 27 gsm; the web may be spunbonded or a bonded carded web. Optionally, the bodyside liner 42 may be treated with a surfactant to increase the wettability of the liner material.

Alternatively, the bodyside liner 42 may also be stretchable, and in some aspects it may be elastomeric. For instance, the liner 42 can be a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued Apr. 22, 2003, to Roessler et al., which is incorporated by reference herein to the extent that it is consistent (i.e., not in conflict) herewith.

The absorbent body 44 is suitably compressible, conformable and capable of absorbing and retaining liquid body exudates released by the wearer. For example, the absorbent chassis can include a matrix of absorbent fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The absorbent body 44 can be in a variety of shapes and configurations as are known in the art, such as rectangular, hourglass shaped, I-shaped, and the like. In addition, the absorbent body 44 can have a density within the range of about 0.10 to about 0.5 grams per cubic centimeter and may be wrapped or encompassed by a suitable tissue or nonwoven wrap for maintaining the integrity and/or the shape of the absorbent chassis.

In one aspect, the absorbent body 44 may be stretchable so as not to inhibit the stretchability of other components to which the absorbent body may be adhered, such as the outercover 40 and/or the bodyside liner 42. For example, the absorbent body may include materials disclosed in U.S. Pat. Nos. 5,964,743, 5,645,542, 6,231,557, 6,362,389, and international patent application WO 03/051254, the disclosure of each of which is incorporated by reference herein.

In some aspects, a surge management layer (not shown) may be included in the diaper 20. The surge management layer may be positioned in the diaper 20 in a variety of locations as is known in the art. For example, the surge management layer can be proximate the absorbent body 44, for example between the absorbent body 44 and the bodyside liner 42, and attached to one or more components of the diaper 20 by methods known in the art, such as by adhesive, ultrasonic bonding, pressure bonding, thermal bonding, and the like or combinations thereof.

A surge management layer helps to decelerate and diffuse surges or gushes of liquid that may be rapidly introduced into the absorbent body 44. Desirably, the surge management layer can rapidly accept and temporarily hold the liquid prior to releasing the liquid into the storage or retention portions of the absorbent body 44. Examples of suitable surge management layers are described in U.S. Pat. No. 5,486,166 and U.S. Pat. No. 5,490,846, the contents of which are incorporated herein by reference to the extent that they are consistent (i.e., not in conflict) herewith.

As mentioned above, the various aspects of the diaper 20 of the present invention can also include a first ear 34 and optionally a second ear 134 (FIGS. 1-6). The first and second ears 34 and 134 may be joined to the absorbent chassis 32 on the inner surface 28 of the diaper 20 (FIGS. 1-6), the outer surface 30 of the diaper 20, or can be sandwiched between at least some of the layers that can make up the absorbent chassis 32, such as the outercover 40 and liner 42. Moreover, the first and second ears 34, 134 may be attached in various combinations. For example, the first ear 34 can be joined to the absorbent chassis 32 on the inner surface 28 of the diaper 20 while the second ear 134 can be joined to the absorbent chassis 32 on the outer surface 30 of the diaper 20.

The ears 34 and 134 can be of various shapes and designs as are known in the art. For example, the ears 34 and 134 can be rectangular, triangular, or have complementary shapes such that they may be removed from a single web of material with little or no trim waste. Suitable ear configurations are described in the previously incorporated U.S. Pat. No. 5,496, 298 issued Mar. 5, 1996, to Kuepper et al.; and in U.S. patent application Ser. No. 11/116,654, entitled ABSORBENT ARTICLE HAVING FRONT AND BACK EARS filed in the name of Van Dyke, the disclosure of which is hereby incorporated by reference to the extent that it is consistent (i.e., not in conflict) herewith.

Figure 2:
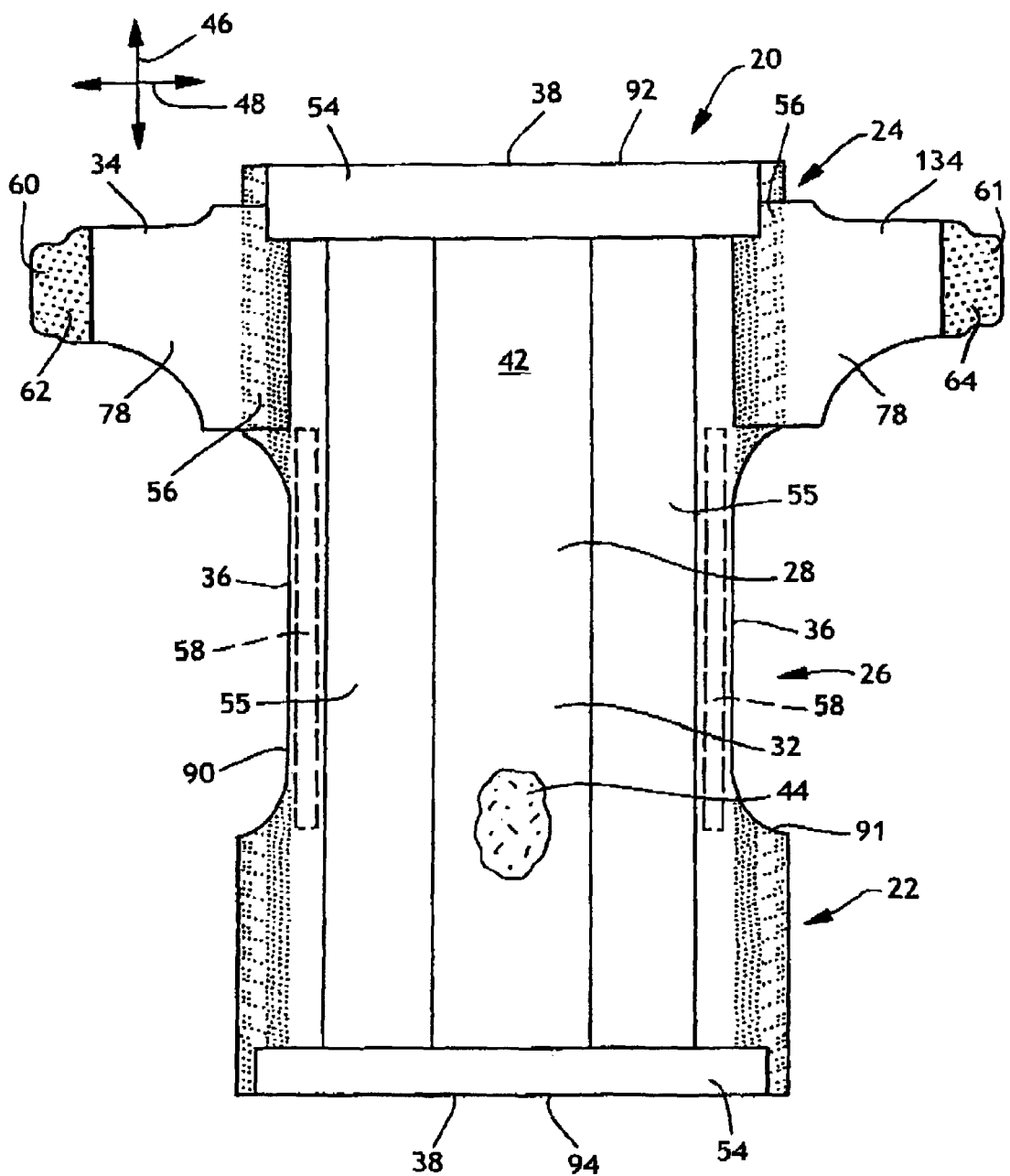
FIG. 2 representatively illustrates a plan view of a diaper similar to that of FIG. 1 in an unfastened, stretched and laid flat condition, and showing the surface of the diaper that faces the wearer with portions cut away to show underlying features.
Figure 3:
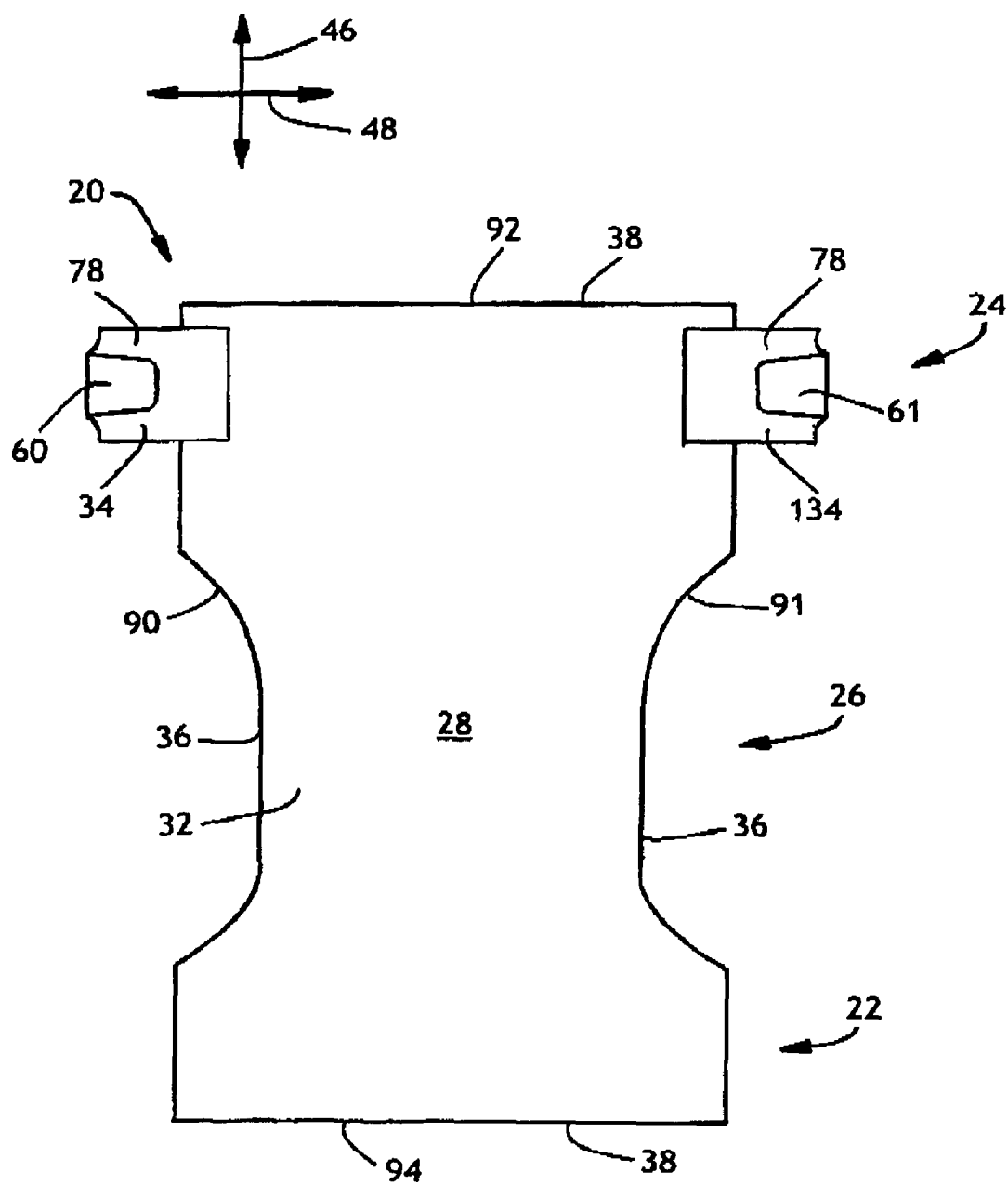
FIG. 3 representatively illustrates a plan view of a diaper similar to that of FIGS. 1 and 2 with components omitted for clarity.

The ears 34 and 134 of the present invention can include and/or be formed from a base material 78 (FIGS. 1-3). The base material 78 may be provided by materials as are known in the art such as woven materials, nonwoven materials, or combinations thereof. In a particular aspect, at least a portion of the base material 78 is an elastomeric material capable of elongating in at least the lateral direction 48 to provide elastomeric ears 34 and 134. Examples of a suitable elastomeric material for use in connection with the base material 78 are a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith. As is known in the art, the base material 78 can optionally include non-stretchable materials or stretchable but inelastic materials. For example, the base material 78 can include various non-stretchable nonwovens such as a spunponded material or a spunbond/meltblown/spunbond (SMS) material. Alternatively, the base materials 78 can include film materials that could also be suitable for use in connection with the outercover 40. In yet another alternative, the base material 78 can include combinations of various stretchable materials and/or nonstretchable materials.

Suitable source webs for the ears 34, 134 are described in U.S. patent application Ser. No. 11/116,655, entitled COMPOSITE WEB filed in the name of Van Dyke, incorporated herein by reference to the extent that it is consistent (i.e., not in conflict) herewith.

As representatively illustrated in FIGS. 1-6, the first ear 34 can optionally include a first fastening member 60 disposed on the first ear 34. Likewise, the second ear 134 can optionally include a second fastening member 61 disposed on the second ear 134. The fastening members 60 and 61 can be disposed on the base material 78 of the ears 34 and 134 or the fastening members 60 and 61 can be in the form of a separate tab that extends from the base material 78 of the ears 34 and 134.

The first fastening member 60 can define a first active fastening portion 62. Likewise the second fastening member 61 can also define a second active fastening portion 64. As can be readily appreciated, the active fastening portions 62 and 64 can be all or a substantial portion of their respective fastening member 60 and 61. Alternatively, the active fastening portions 62 and 64 can optionally be only a segment of their respective fastening member 60 and 61.

The active fastening portions 62 and 64 can include any refastenable fastener material suitable for absorbent articles, such as adhesive fastening material, cohesive fastening material, mechanical fastening material, or the like. In one aspect of the invention, the active fastening portions 62 and 64 are hook fastening material that can include various forms of interlocking geometric-shaped materials that are intended to engage another material such as hooks, bulbs, mushrooms, arrowheads, balls on stems, male mating components or the like. One specific example of a fastening member is VELCRO HTH 858 or VELCRO HTH 823 available from Velcro Industries B.V., Amsterdam, Netherlands.

The fastening members 60, 61 may be arranged on the ears 34, 134 to engage different portions of the diaper 20. For example, the fastening members 60, 61 can be configured to engage the outer surface 30 of the diaper 20. In such a configuration, the fastening members 60, 61 can be attached to the ears 34, 134 on the inner surface 28 of the diaper 20. Alternatively, the fastening members 60, 61 attached to the ears 34, 134 can be configured to engage the inner surface 28 of the diaper 20. In such a configuration, the fastening members 60, 61 can be attached to the ears 34, 134 on the outer surface 30 of the diaper 20.

Accordingly, the active fastening portions 62 and 64 of the fastening members 60, 61 on the ears 34, 134 may be configured to refastenably engage directly with the outercover 40 or the liner 42 of the diaper 20. Alternatively, at least one attachment panel (not shown) may be suitably located on the diaper 20 to which the active fastening portions 62 and 64 of the fastening members 60, 61 on the ears 34, 134 are configured to engage. For example, an attachment panel can be located on the outercover 40.

Thus, the fastening members 60, 61 can be employed to attach the back waist region 24 of the diaper 20 to the front waist region 22 of the diaper 20 about the waist of the wearer. Accordingly, the waist edges 38 of the diaper 20 are configured to encircle the waist of the wearer to define the waist opening 50 of the diaper, while the article side edges 36 of the diaper 20 define the leg openings 52 (FIG. 1).

The active fastening portions 62 and 64 of the present invention can be arranged in various configurations for improved performance during processing and/or packaging. For example, as representatively illustrated in FIG. 3, the first active fastening portion 62 can be in an overlaid relationship with the inner surface 28 on the first ear 34. Likewise, the second active fastening portion 64 can be in an overlaid relationship with the inner surface 28 on the second ear 134. As such, the active fastening portions 62 and 64 are isolated from the environment around the diaper 20 until the user or the caregiver wishes to expose them for use.

Figure 4:
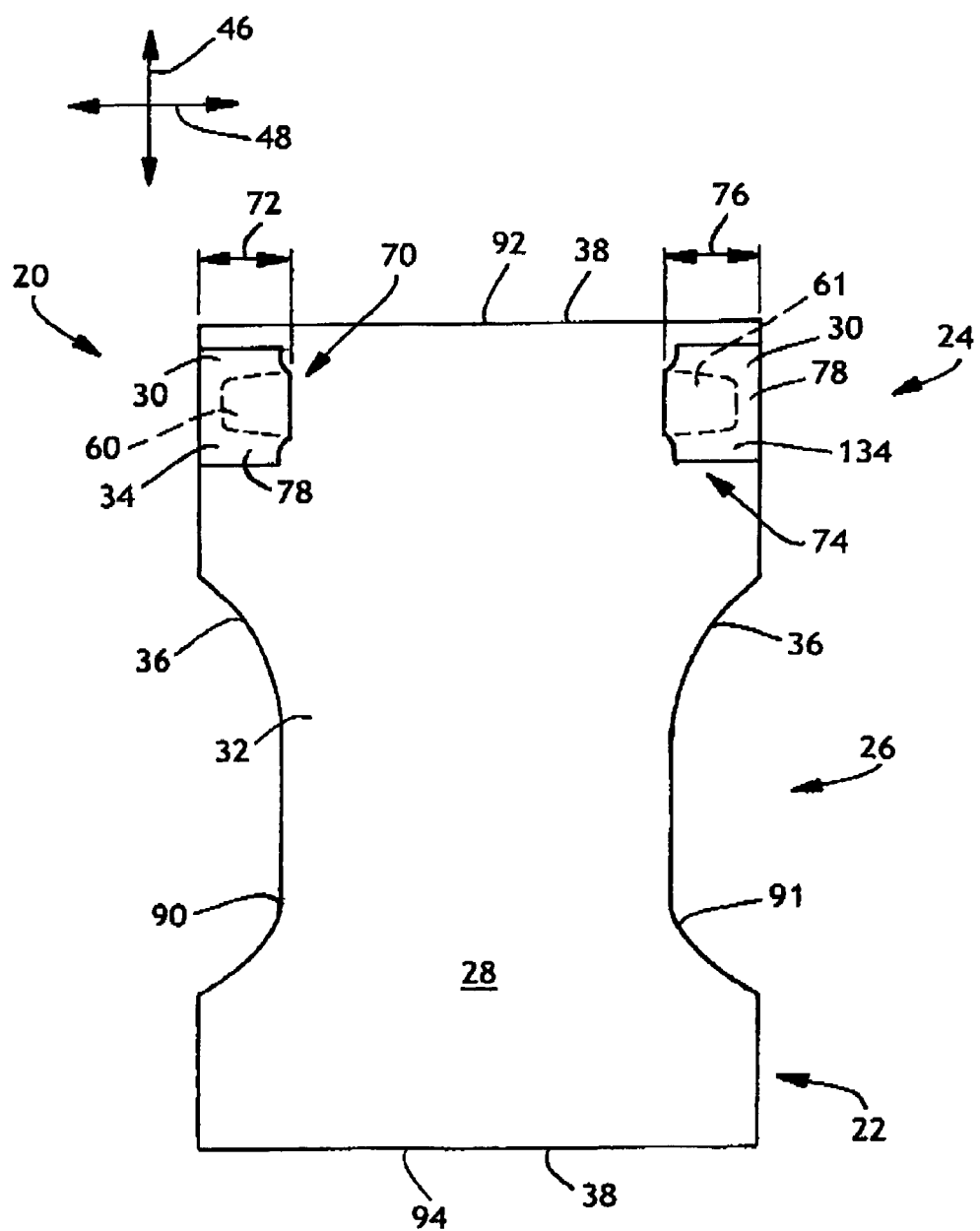
FIG. 4 representatively illustrates a plan view of the diaper of FIG. 3 with portions of the diaper folded.

As representatively illustrated in FIGS. 4-6A, to shield the first fastening member 60, the diaper 20 can further include a first inboard fold 70. In such a configuration, the first fastening member 60 can be in an overlaid relationship with the inner surface 28 on the absorbent chassis 32 proximate the first chassis side edge 90 (FIG. 4). In addition, as representatively illustrated in FIGS. 4-6A, the first inboard fold 70 can define a first inboard fold width in the lateral direction 48, indicated at the arrow marked 72.

Likewise, the diaper 20 can also include a second inboard fold 74 to shield the second fastening member 61. In such a configuration, the second fastening member 61 can be in an overlaid relationship with the inner surface 28 on the absorbent chassis 32 proximate the second chassis side edge 91 (FIGS. 4-6A). In addition, as representatively illustrated in FIGS. 4-6A, the second inboard fold 74 can define a second inboard fold width in the lateral direction 48, indicated at the arrow marked 76.

Figures 6, 6A:
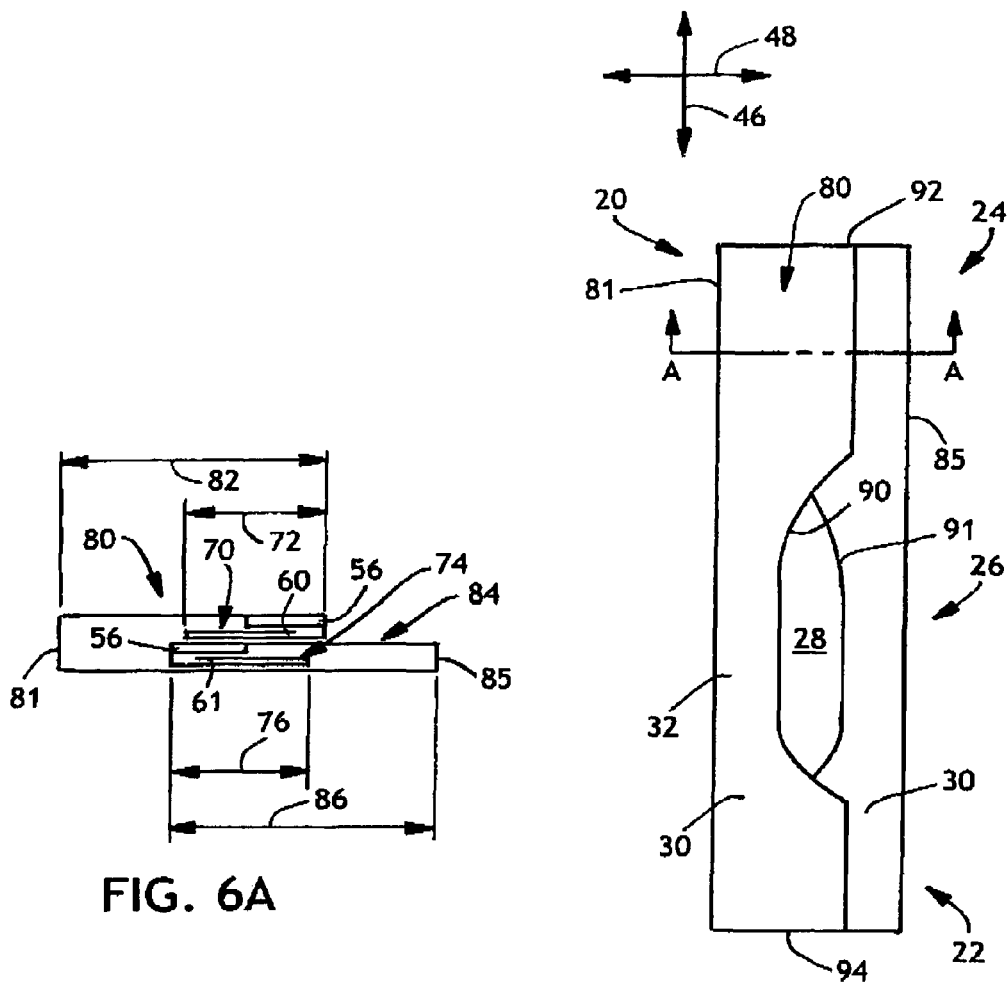
FIG. 6 representatively illustrates a plan view of the diaper of FIG. 3 with portions of the diaper folded.
FIG. 6A representatively illustrates a section view taken at line A-A in FIG. 6.

Still further, as representatively illustrated in FIGS. 6 and 6A, the diaper 20 can include a first interior fold 80. The first interior fold 80 can define a first interior fold axis 81. The first interior fold axis 81 can be located inboard of the first chassis side edge 90. In addition, the first interior fold 80 can define a first interior fold width in the lateral direction 48 indicated at the arrow marked 82. In particular aspects, the first interior fold width 82 can be as wide as the first inboard fold width 72, and suitably the first interior fold width 82 can be wider than the first inboard fold width 72 (FIGS. 6, 6A) to minimize any creasing of the fastener member 60 and/or the ear 34.

Accordingly, in such an aspect, the first ear 34, the first fastener member 60 and the first active fastening portion 62 can be isolated by the absorbent chassis 32 from the environment both during processing and within the package. As such, these elements (i.e., the first ear 34, the first fastener member 34 and the first active fastening portion 62) may be less likely to be undesirably creased, which can diminish the performance of the first active fastening portion 62 and result in a less attractive product for the user and/or caregiver.

Figures 5, 5A:
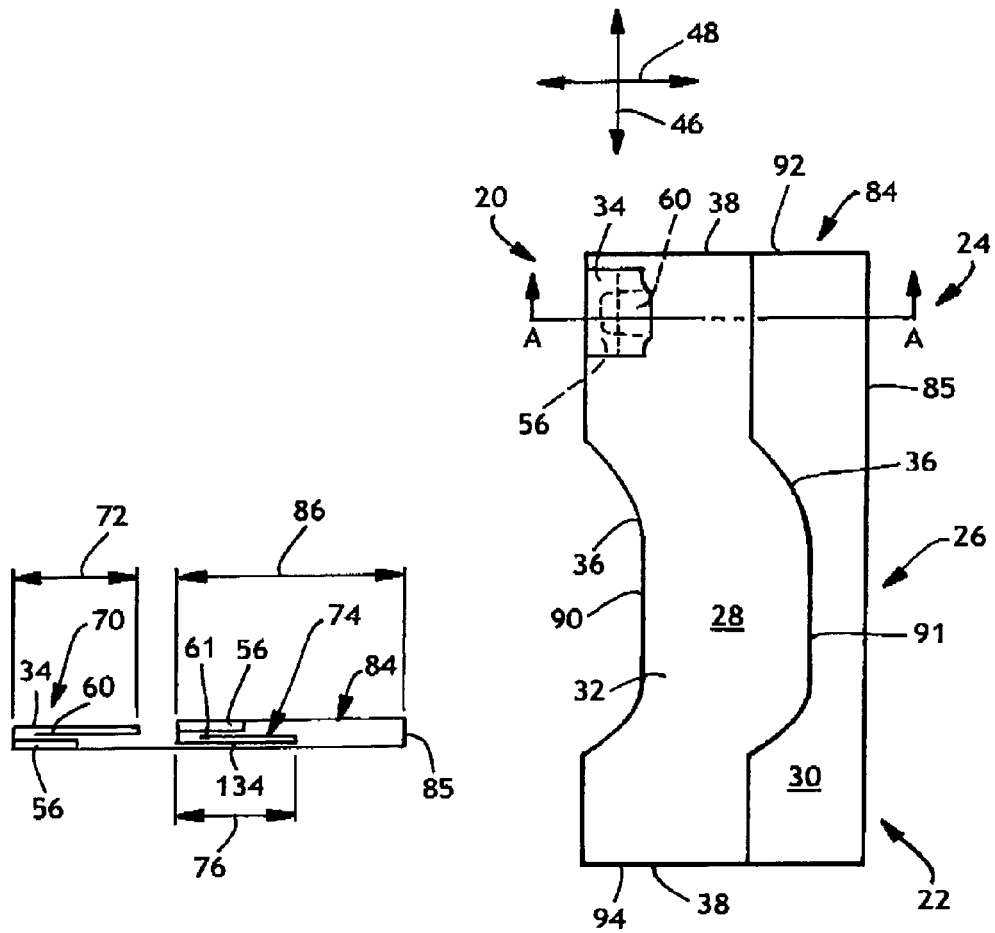
FIG. 5 representatively illustrates a plan view of the diaper of FIG. 3 with portions of the diaper folded.
FIG. 5A representatively illustrates a section view taken at line A-A in FIG. 5.

Similarly, as representatively illustrated in FIGS. 5-6A, the diaper 20 can include a second interior fold 84. The second interior fold 84 can define a second interior fold axis 85. The second interior fold axis 85 can be located inboard of the second chassis side edge 91. In addition, the second interior fold can define a second interior fold width in the lateral direction 48 indicated at the arrow marked 86. In particular aspects, the second interior fold width 86 can be as wide as the second inboard fold width 76, and suitably the second interior fold width 86 can be wider than the second inboard fold width 76 (FIGS. 5, 5A, 6, 6A). Further, as representatively illustrated in FIGS. 6 and 6A, the combination of the first interior fold 80 and the second interior fold 84 can optionally place the first ear 34 in an overlaid relationship with the second ear 134.

Accordingly, the second ear 134, the second fastener member 61 and the second active fastening portion 64 can be isolated by the absorbent chassis 32 from the environment both during processing and within the package. As such, these elements (i.e., the second ear 134, the second fastener member 61 and the second active fastening portion 64) may be less likely to be undesirably creased, which can diminish the performance of the second active fastening portion 64 and result in a less attractive product for the user and/or caregiver.

As representatively illustrated in FIGS. 4-6, the various folds of the present invention can be substantially parallel for improved performance and ease of manufacturing. For example, the first inboard fold 70, the first interior fold 80, the second inboard fold 74 and the second interior fold 84 can all be substantially parallel. Moreover, the various folds can also extend substantially in the longitudinal direction 46. For example, the first inboard fold 70, the first interior fold 80, the second inboard fold 74 and the second interior fold 84 can each extend substantially in the longitudinal direction 46 (FIGS. 4-6).

As such, the diaper 20 of the present invention can, in certain configurations, include a plurality of longitudinally extending folds 70, 74, 80 and 84. As a result, the outer surface 30 on the first fastening member 34 can be in an overlaid relationship with the inner surface 28 on the absorbent chassis 32 proximate the first chassis side edge 90 (FIGS. 6, 6A). In addition, the first ear 34 can be sandwiched by said inner surface 28 of said absorbent chassis 32 (FIGS. 6 and 6A).

Further, the outer surface 30 on the second fastening member 61 can be in an overlaid relationship with the inner surface 28 on the absorbent chassis 32 proximate the second chassis side edge 91 (FIGS. 5A and 6A). In addition, the second ear 134 can be sandwiched by the inner surface 28 of the absorbent chassis 32 (FIGS. 6, 6A).

As mentioned above, the arrangement of the ears 34 and 134 and fastening members 60 and 61 as described above can advantageously provide a diaper 20 where the ears 34, 134 and fastening members 60, 61 are isolated by the absorbent chassis 32 from the environment surrounding the diaper 20. The advantages mentioned above resulting from the various configurations of the present invention can be particularly desirable where the ears 34 and 134 are at least partially elastomeric. That is, elastomeric ears can, in certain circumstances, be soft and limp and as such can be susceptible to unsightly crumpling during processing and packaging. Further, active fastening portions 62 and 64 that are mechanical fastening materials, and in particular hook material, can be relatively rigid, and as such susceptible to creasing during processing and packaging. Such creasing, in addition to being unattractive, can reduce the ability of the fastening member 60, 61 to engage and maintain engagement as desired during use.

Figure 7:
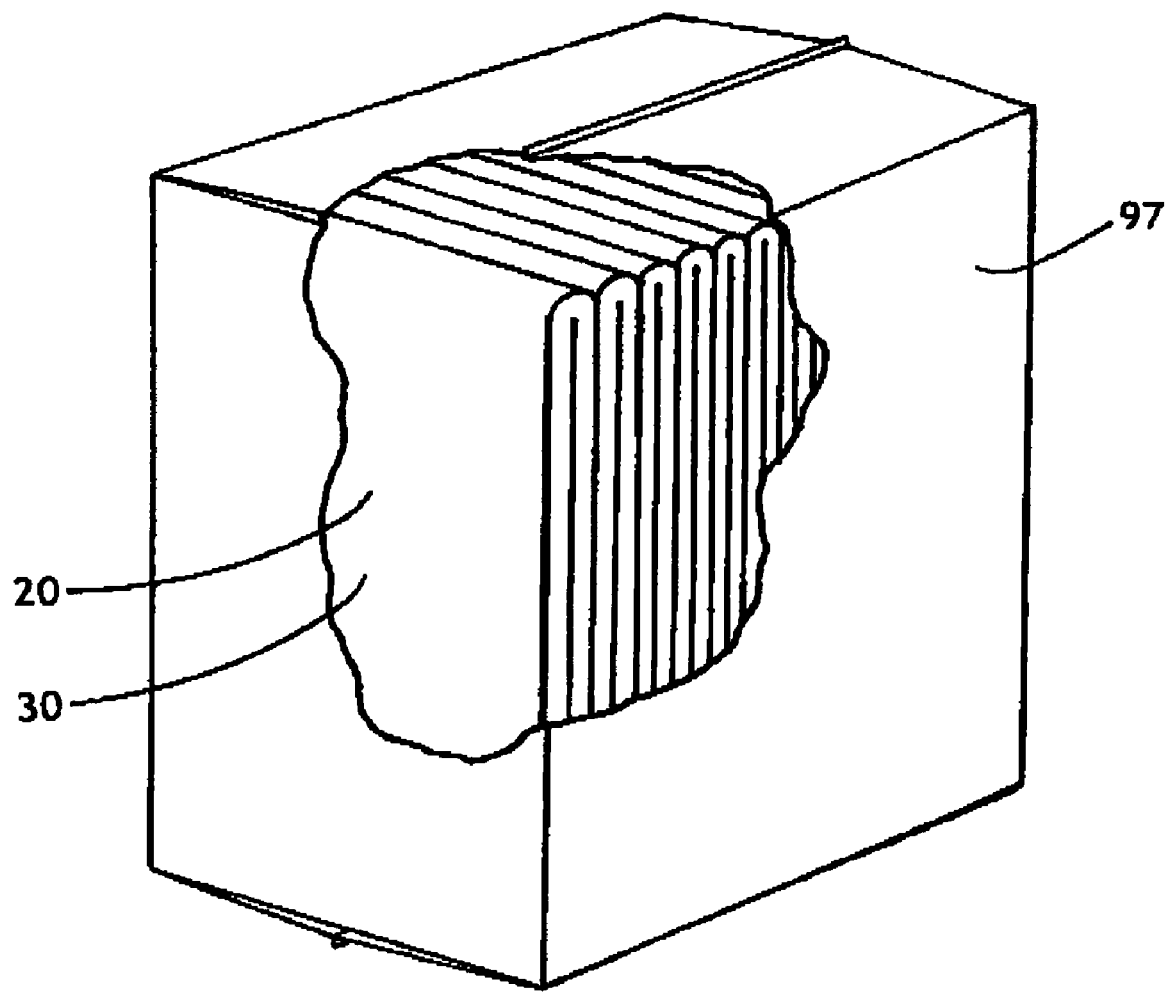
FIG. 7 representatively illustrates a perspective view of a package of diapers, with portions of the package cut away to show the diapers therein.

Turning now to FIG. 7, the present invention is also directed to a package 97 that contains a plurality of the diapers 20 as described above and illustrated in FIGS. 1-6A. The package 97 can contain at least three diapers 20, and suitably can contain from 10 to 96 or more diapers 20. Packaging suitable for use with the diaper 20 is well known in the art and for example is described in U.S. Pat. No. 6,318,555 issued Nov. 20, 2001, to Kuske et al., the disclosure of which is hereby incorporated by reference to the extent that it is consistent (i.e., not in conflict) herewith.

The package 97 can be suitably provided by a polymer film material that is sufficiently flexible to assume a generally hexahedral shape when the package 97 is filled with diapers 20. Alternatively, other suitable materials or shapes may be utilized for the package 97 as are known in the art.

Accordingly, while various diaper configurations can conceivably randomly result when the ears 34 and 134 and fastening members 60 and 61 are folded and placed in a package 97, diaper configurations of the present invention as described above that are suitably repeated in each diaper 20 within the package 97 can advantageously provide the user and the caregiver with a consistent, pleasing product experience.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A folded absorbent article defining a lateral direction and a longitudinal direction perpendicular to said lateral direction, an inner surface and an outer surface opposite said inner surface, said folded absorbent article comprising:

An absorbent chassis defining a chassis back waist edge and a chassis front waist edge opposite said chassis back waist edge, a first chassis side edge extending in said longitudinal direction and a second chassis side edge extending in said longitudinal direction opposite said first chassis side edge, said absorbent chassis comprising:
A liquid impermeable outercover; and
An absorbent body disposed on said outercover;
A first ear formed separately from and attached proximate said first chassis side edge;
A first fastening member defining a first active fastening portion, said first fastening member disposed on said first ear, wherein said first active fastening portion is in an overlaid relationship with said inner surface on said first ear;
A first inboard fold wherein said first fastening member is in an overlaid relationship with said inner surface on said absorbent chassis proximate said first chassis side edge, and defining a first inboard fold width in said lateral direction; and
A first interior fold defining a first interior fold axis inboard of said first chassis side edge, and a first interior fold width in said lateral direction, wherein said first interior fold width is at least as wide as said first inboard fold width.

2. The folded absorbent article of claim 1 further comprising:
   A second ear formed separately from and attached proximate said second chassis side edge;
   A second fastening member defining a second active fastening portion, said first fastening member disposed on said second ear; wherein said second active fastening portion is in an overlaid relationship with said inner surface on said second ear;
   A second inboard fold wherein said second fastening member is in an overlaid relationship with said inner surface on said absorbent chassis proximate said second chassis side edge, and defining a second inboard fold width in said lateral direction; and
   A second interior fold defining a second interior fold axis inboard of said second chassis side edge, and a second interior fold width in said lateral direction, wherein said second interior fold width is at least as wide as said second inboard fold width.

3. The folded absorbent article of claim 2 wherein said first interior fold and said second interior fold places said first ear in an overlaid relationship with said second ear.

4. The folded absorbent article of claim 2 wherein said first inboard fold, said second inboard fold, said first interior fold and said second interior fold are all substantially parallel.

5. The folded absorbent article of claim 2 wherein said first inboard fold, said second inboard fold, said first interior fold and said second interior fold all extend substantially in said longitudinal direction.

6. The folded absorbent article of claim 1 wherein said first ear is elastomeric.

7. The folded absorbent article of claim 1 wherein said first active fastening portion is a mechanical fastening material.

8. A package of absorbent articles comprising:
   a package; and
   a plurality of absorbent articles, each of said absorbent articles defining a lateral direction and a longitudinal direction perpendicular to said lateral direction, an inner surface and an outer surface opposite said inner surface, each of said absorbent articles comprising:
   An absorbent chassis defining a chassis back waist edge and a chassis front waist edge opposite said chassis back waist edge, a first chassis side edge extending in said longitudinal direction and a second chassis side edge extending in said longitudinal direction opposite said first chassis side edge, said absorbent chassis comprising:
   A liquid impermeable outercover; and
   An absorbent body disposed on said outercover;
   A first ear formed separately and attached proximate said first chassis side edge;
   A first fastening member defining a first active fastening portion, said first fastening member disposed on said first ear; wherein said first active fastening portion is in an overlaid relationship with said inner surface on said first ear;
   A first inboard fold wherein said first fastening member is in an overlaid relationship with said inner surface on said absorbent chassis proximate said first chassis side edge, and defining a first inboard fold width in said lateral direction; and
   A first interior fold defining a first interior fold axis inboard of said first chassis side edge, and a first interior fold width in said lateral direction, wherein said first interior fold width is at least as wide as said first inboard fold width.

9. The package of claim 8 wherein said package contains at least ten said absorbent articles.

10. The package of claim 8 wherein each of said absorbent articles further comprise:
    A second ear formed separately from and attached proximate said second chassis side edge;
    A second fastening member defining a second active fastening portion, said first fastening member disposed on said second ear; wherein said second active fastening portion is in an overlaid relationship with said inner surface on said second ear;
    A second inboard fold wherein said second fastening member is in an overlaid relationship with said inner surface on said absorbent chassis proximate said second chassis side edge, and defining a second inboard fold width in said lateral direction; and
    A second interior fold defining a second interior fold axis inboard of said second chassis side edge, and a second interior fold width in said lateral direction, wherein said second interior fold width is at least as wide as said second inboard fold width.

11. The package of claim 10 wherein said first interior fold and said second interior fold places said first ear in an overlaid relationship with said second ear in each of said absorbent articles.

12. The package of claim 10 wherein said first inboard fold, said second inboard fold, said first interior fold and said second interior fold are all substantially parallel in each of said absorbent articles.

13. The package of claim 10 wherein said first inboard fold, said second inboard fold, said first interior fold and said second interior fold all extend substantially in said longitudinal direction in each of said absorbent articles.

14. The package of claim 8 wherein said first ear is elastomeric in each of said absorbent articles.

15. The package of claim 8 wherein said first active fastening portion is a mechanical fastening material.

16. A folded absorbent article defining a lateral direction and a longitudinal direction perpendicular to said lateral direction, an inner surface and an outer surface opposite said inner surface, said folded absorbent article comprising:
    An absorbent chassis defining a chassis back waist edge and a chassis front waist edge opposite said chassis back waist edge, a first chassis side edge extending in said longitudinal direction and a second chassis side edge extending in said longitudinal, direction opposite said first chassis side edge, said absorbent chassis comprising:
    A liquid impermeable outercover; and
    An absorbent body disposed on said outercover;
    A first ear formed separately from and attached proximate said first chassis side edge;
    A second ear formed separately from and attached proximate said second chassis side edge;
    A first fastening member defining a first active fastening portion, said first fastening member disposed on said first ear;
    A second fastening member defining a second active fastening portion, said second fastening member disposed on said second ear; and
    A plurality of longitudinally extending folds, wherein said outer surface on said first fastening member is in an overlaid relationship with said inner surface on said absorbent chassis proximate said first chassis side edge, and said first ear is sandwiched by said inner surface of said absorbent chassis; and wherein said outer surface on said second fastening member is in an overlaid relationship with said inner surface on said absorbent chassis proximate said second chassis side edge, and said second ear is sandwiched by said inner surface of said absorbent chassis.

17. The folded absorbent article of claim 16 wherein said first interior fold and said second interior fold places said first ear in an overlaid relationship with said second ear.

18. The folded absorbent article of claim 16 wherein said plurality of longitudinally extending folds are all substantially parallel.

19. The folded absorbent article of claim 16 wherein said first ear and said second ear are elastomeric.

20. The folded absorbent article of claim 16 wherein said first active fastening portion and said second active fastening portion are hook materials.

* * * * *